United States Patent
Ou

(10) Patent No.: US 10,465,094 B2
(45) Date of Patent: Nov. 5, 2019

(54) METHOD OF APPLYING RAPID CURE SILICONE LUBRICIOUS COATINGS

(71) Applicant: Ethicon, Inc., Somerville, NJ (US)

(72) Inventor: Duan Li Ou, Warren, NJ (US)

(73) Assignee: Ethicon, Inc., Somerville, NJ (US)

( * ) Notice: Subject to any disclaimer, the term of this patent is extended or adjusted under 35 U.S.C. 154(b) by 117 days.

(21) Appl. No.: 15/372,509

(22) Filed: Dec. 8, 2016

(65) Prior Publication Data

US 2018/0163090 A1 Jun. 14, 2018

(51) Int. Cl.
*B05D 3/06* (2006.01)
*C09D 183/14* (2006.01)
(Continued)

(52) U.S. Cl.
CPC ............ *C09D 183/14* (2013.01); *A61B 34/30* (2016.02); *A61L 31/06* (2013.01); *A61L 31/10* (2013.01);
(Continued)

(58) Field of Classification Search
CPC ...... C09D 183/04; B05D 3/065; B05D 3/068; A61L 31/16
(Continued)

(56) References Cited

U.S. PATENT DOCUMENTS 3,775,452 A 11/1973 Karstedt
3,814,730 A 6/1974 Karstedt
(Continued)

FOREIGN PATENT DOCUMENTS

| EP | 0111829 A | 6/1984 |
|---|---|---|
| EP | 0227340 A | 7/1987 |
| WO | 2014/163928 | 10/2014 |

OTHER PUBLICATIONS

Database CA [Online] Chemical Abstracts Service, retrieved from STN-Internatinal accession No. 68:72249 CA & K. Sato Et Al., "Radiation sterilization of medical devices and supplies. I. Disposable syringes and needles", Eisei Kagaku vol. 13, No. 3, 1967, pp. 136-139 (Abstract).

(Continued)

*Primary Examiner* — Cachet I Sellman

(57) ABSTRACT

A silicone coating process that improves the durability of silicone coatings on the surfaces of surgical needles and other medical devices. The silicone coated surgical needles or medical devices produced by this process have both superior lubricity and durability for ease of repeated and successive passes through tissue. The coating compositions used in the novel process contain an excess amount of polymethylhydrosiloxane cross-linker. After curing, the process utilizes gamma radiation to treat the lubricious coatings. The coatings have improved durability and performance. The penetration performance of needles coated by this novel method remains constant and flat over at least one hundred repeat passes through tissue or tissue simulation media. This provides a consistent or flat tactile response from the needles to the hand of the surgeon during a lengthy closure process, rather than an unpredictably increasing force profile. The process is also advantageous to coat reusable instruments, robotic instruments, and instruments used in minimally invasive procedures.

22 Claims, 1 Drawing Sheet

Penetration performance of gamma irradiated Example 2b comparing to gamma irradiated Nusil MED 4162 coated 16mil RB-1 needles and uncoated 16mil RB-1 needles (the raw data is show in Table 2-2)

(51) Int. Cl.
*A61L 31/10* (2006.01)
*A61L 31/06* (2006.01)
*A61L 31/14* (2006.01)
*A61B 34/30* (2016.01)
*A61M 5/32* (2006.01)

(52) U.S. Cl.
CPC ............. *A61L 31/14* (2013.01); *A61M 5/329* (2013.01); *A61L 2300/606* (2013.01); *A61L 2400/10* (2013.01); *A61L 2420/02* (2013.01); *A61L 2420/06* (2013.01)

(58) Field of Classification Search
USPC ........................................................ 427/428
See application file for complete search history.

(56) References Cited

U.S. PATENT DOCUMENTS

| 5,776,268 | A | 7/1998 | McJames et al. | |
|---|---|---|---|---|
| 7,943,697 | B2* | 5/2011 | Simon | A61L 2/081 250/427 |
| 8,883,245 | B2 | 11/2014 | Cichocki et al. | |
| 9,434,857 | B2 | 9/2016 | Ou | |
| 2004/0209784 | A1* | 10/2004 | Hardman | A61L 29/085 508/204 |
| 2005/0203201 | A1* | 9/2005 | Steube | A61L 31/10 522/15 |
| 2007/0089557 | A1* | 4/2007 | Solomon | B25J 9/1045 74/490.01 |
| 2008/0071228 | A1* | 3/2008 | Wu | A61L 31/10 604/234 |
| 2009/0010985 | A1* | 1/2009 | Sakhrani | B05D 5/08 424/422 |
| 2009/0204022 | A1* | 8/2009 | Schwindt | A61B 10/0283 600/566 |
| 2012/0083680 | A1* | 4/2012 | Carr | A61B 5/0492 600/373 |
| 2013/0122314 | A1* | 5/2013 | Ou | A61L 29/085 428/429 |

OTHER PUBLICATIONS

International Search Report and Written Opinion dated Mar. 5, 2018, for international application PCT/US2017/061290.

* cited by examiner

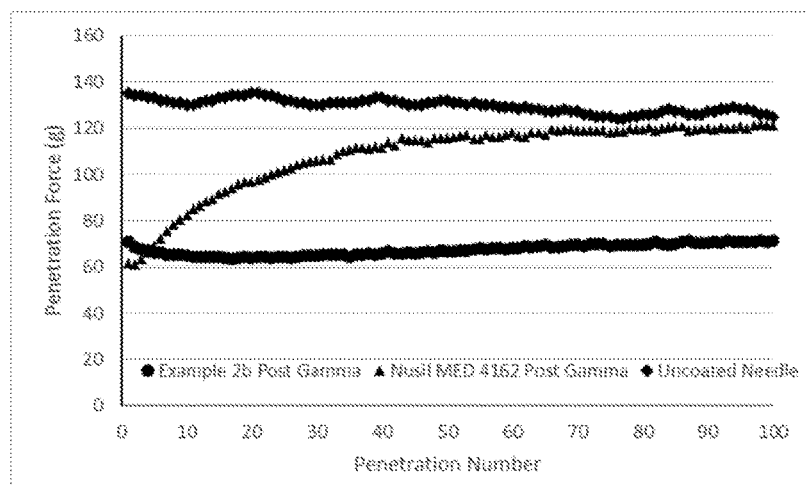
Penetration performance of gamma irradiated Example 2b comparing to gamma irradiated Nusil MED 4162 coated 16mil RB-1 needles and uncoated 16mil RB-1 needles (the raw data is show in Table 2-2)

METHOD OF APPLYING RAPID CURE SILICONE LUBRICIOUS COATINGS

TECHNICAL FIELD

The field of art to which this invention pertains is methods of applying silicone-based lubricious coatings, in particular, methods and processes for applying silicone-based lubricious coatings for use on surfaces of medical devices such as surgical needles.

BACKGROUND OF THE INVENTION

Lubricious coatings are typically required for implantable or insertable medical devices such as hypodermic needles, surgical needles, catheters, and cutting devices that contact tissue. The primary purpose of such coatings is to ease the penetration or insertion of the device into and through tissue, thereby facilitating a surgical procedure.

A number of conventional, biocompatible lubricants have been developed for such applications, and they are typically silicone (e.g., polydimethylsiloxane) or silicone-containing coatings. For example, condensation-cured silicone coatings are known to be useful as lubricious coatings on medical devices. Such coating formulations contain amino and alkoxyl functional groups, which can be cured (cross-linked) at relatively low temperatures and high humidity levels. It is also known to use an aminopropyl-containing silicone as a lubricious coating for syringe needles. Those coatings use an epoxy-containing silicone as a cross-linking agent and may have improved penetration performance with multiple penetrations. It is also known to utilize thermoplastic polymers such as polypropylene (e.g., in powder form) in blends of silicone solutions to improve the mechanical properties of the resulting coating layers. The polypropylene powders may increase the durability of silicone needle coatings without sacrificing lubricity. Most of the known and conventionally used silicone coatings listed above require a lengthy thermal curing step after application, which is quite often unsuitable for rapid, high speed production processes.

Attempts have been made to improve coating cure times including rapid UV curable silicone lubricious coatings that can be cured rapidly (<10 seconds) on a medical device, such as needle, after UV light exposure. However, the potential hazard of certain UV curable components typically contained in such coatings may provide cause for concern.

Karstedt of GE Silicone invented a highly active platinum catalyst for hydrosilylation at the beginning of the 1970's (U.S. Pat. No. 3,775,452). The "Karstedt catalyst" is highly active at ambient temperature, and this quality makes it difficult to use in most commercial silicone coatings without the addition of an inhibitor. Several other platinum catalysts had been subsequently invented attempting to address this problem. For example, platinum-cyclovinylmethylsiloxane complex was made immediately after the invention of the Karstedt catalyst (U.S. Pat. No. 3,814,730), and this catalyst is purported to provide longer production process pot life for a vinyl/hydride reactive coating solution mixture. Platinum tetramethyldivinylsiloxane dimethyl maleate and platinum tetramethyldivinylsiloxane dimethyl fumarate were disclosed in the mid-1990's, both of which are claimed to provide longer production process pot life for vinyl/hydride coating solution mixtures. Both of those catalysts are still commonly used in the silicone coating industry.

In order to be useful on medical devices such as surgical needles, it is critical that lubricious silicone coatings be durable and easy to apply in a uniform, consistent manner. A surgical procedure in which tissue is approximated or closed with surgical sutures typically requires multiple passes of the surgical needle and suture through tissue. Ease of penetration over multiple passes through tissue will make the surgeon's job easier and this will likely result in a better tissue repair or closure. The patient will benefit not only by enhanced healing and superior outcome, but also by a faster procedure resulting in a shorter time for possible exposure of the wound or opening to pathogens in the environment, and also by requiring a shorter period of time that the patient is under general anesthesia, when anesthesia is required.

Surgical needles are typically manufactured in high speed production processes. For example, U.S. Pat. No. 5,776,268, incorporated by reference, discloses such processes. After the needles are formed and shaped (typically from wire stock), the in-process needles are cleaned, and the needles are coated with lubricious coatings in a conventional manner such as by dipping, spraying, brushing, etc. After application of the coatings in a uniform manner to substantially coat the exterior surfaces of the needles, the needles are then moved into appropriate curing equipment, such as an oven, for a coating curing process wherein energy (e.g., thermal) is provided to cure the silicone coatings.

Silicone coatings are typically prepared at the manufacturing site by mixing the silicone polymer components with a suitable catalyst and solvents. Such coatings and catalysts, especially when of medical grade for use on medical devices, are expensive and typically have what is conventionally known in this art as a short "pot life". The term pot life, as conventionally used in the art, has the meaning that the silicone coatings when mixed with catalyst and ready for application in a coating process typically have a limited amount of time in which they are useful because of cross-linking that occurs at ambient conditions in the production facility. Such short pot life can result in a number of known problems including, for example, premature curing, leading to a viscosity increment of the coating solution during the time of its usage. This will typically cause inconsistencies in the resulting coating on the surface of the medical device, resulting in both visual and performance deficiencies and product defects.

Novel rapid cure silicone coatings utilizing novel platinum catalysts are disclosed in U.S. Pat. No. 9,434,857. The coatings are referred to as command-cure coatings that cure rapidly when exposed to heat, and which also have extended pot life.

Although the silicone coatings and coated needles of the prior art provide benefits with regard to lubricity and durability, there remains a need in this art for improved silicone coatings for medical devices that have improved lubricity and durability for multiple uses and multiple passes through tissue. The needles of the prior art may lose a degree of lubricity over the course of 100 or so passes through tissue which is typical of the suturing of a large or complex wound. Also, the penetration profile may change over the course of the suturing so that the surgeon experiences a different or increasing penetration force profile over the course of the suturing and wound closure procedure. This may affect the efficacy of the wound closure. It is known that a flat penetration force profile will produce a superior result. Therefore, there is a need for silicone coated needles having a flat penetration force profile. There is also a need for durable silicone coatings for medical devices useful with robotic instruments, as well as a need for such coatings on reusable devices.

SUMMARY OF THE INVENTION

Accordingly, a novel method of coating medical devices, including surgical needles, with lubricious silicone coating compositions is disclosed. The surgical needles produced by this novel method have a flat penetration force profile. In the novel method of the present invention, a medical device having a surface is coated with a lubricous silicone coating composition. The coating composition contains a first cross-linkable silicone polymer having first reactive functionalities, a siloxane cross-linking agent having second reactive functionalities, and about 10 wt. % to about 90 wt. % of a second non-cross-linkable silicone polymer based on total solids. The second non-cross-linkable silicone polymer has a weight average molecular weight between about 400,000 and 10,000,000. The coating compositions also contains a platinum catalyst. The coating composition contains an excess amount of the siloxane cross-linking agent. The excess amount is about 0.2 wt. % to about 6 wt. % of the silicone cross-linking agent, based on total solids, wherein said second reactive functionalities are present in excess to said first reactive functionalities. And, the coating contains a catalyst that consists essentially of platinum divinyltetramethyldisiloxane ethynylcyclohexanol complex having the formula:

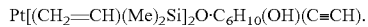

The coating composition has a weight.

The coating is cured by exposure to an energy source, e.g., heat. Then, the cured coating on the surface of the medical device is exposed to gamma radiation for a sufficient period of time to effectively cure the coating composition, thereby providing a coated medical device having a flat penetration force profile.

Another aspect of the present invention is a medical device having a surface, wherein at least part of the surface is coated with a lubricous silicone coating in accordance with the above-described method.

Yet another aspect of the present invention is a surgical needle coated in accordance with the above-described method.

These and other aspects and advantages of the present invention will become more apparent from the following description and accompanying drawings.

BRIEF DESCRIPTION OF THE DRAWINGS

FIG. 1 is a graph showing the penetration performance of gamma irradiated Example 2b needles compared to gamma irradiated Nusil MED 4162 coated needles and uncoated

DETAILED DESCRIPTION OF THE INVENTION

The terms silicone and siloxane are conventionally used interchangeably in this art, and that usage has been adopted herein.

Lubricious Coating Composition

The present invention is directed to novel lubricious silicone coating compositions which are particularly useful for coating surfaces of medical devices such as surgical needles and other tissue piercing or cutting devices and novel methods of applying such coatings. The compositions include a mixture of a cross-linkable siloxane polymer and a non-cross-linkable siloxane polymer, a conventional silicone cross-linking agent, and a platinum catalyst. The silicone polymer components are blended with conventional aromatic organic solvents, including, for example, xylene and aliphatic organic solvents (such as, for example, hexane or its commercial derivatives) to form coating solutions or compositions.

The cross-linkable siloxane polymers useful in the coating compositions of the present invention will have reactive functionalities or terminal functional groups, including but not limited to vinyl terminated, hydroxyl and acrylate functional groups. The cross-linkable siloxane polymers that can be used in the lubricious coatings of the present invention preferably include vinyl terminated polydialkylsiloxane or vinyl terminated polyalkoarylsiloxane. Examples include but are not limited to the following: vinyl terminated siloxane polymers: polydimethyl siloxane, polydiphenylsilane-dimethylsiloxane copolymer, polyphenylmethylsiloxane, polyfluoropropylmethyl-dimethylsiloxane copolymer and polydiethylsiloxane. It is particularly preferred to use vinyl terminated cross-linkable polymethyl siloxane.

The non-cross-linkable siloxanes that can be used in the practice of the present invention include polydimethyl siloxane, polyalkylmethylsiloxane, such as polydiethylsiloxane, polyfluoropropylmethylsiloxane, polyoctylmethylsiloxane, polytetradecylmethylsiloxane, polyoctadecylmethylsiloxane, and polyalkylmethyl dimethylsiloxane, such as polyhexadecymethylsiloxane-dimethyl siloxane. It is particularly preferred to use non-cross-linkable polymethyl siloxanes with weight average molecular weights (Mw) typically in a range of about 400,000 to at least about 1,000,000, more typically about 400,000 to about 10,000,000, and preferably about 400,000 to about 700,000 which are in the form of non-flowable gum having a viscosity greater than 600,000 cps.

The cross-linking agents that can be used in the coatings of the present invention include conventional silicone cross-linking agents such as, for example, polymethylhydro siloxane, polymethylhydro-co-polydimethylsiloxane, polyethylhydrosiloxane, polymethylhydrosiloxane-co-octylmethylsiloxane, polymethylhydrosiloxane-co-methylphenylsiloxane. The cross-linking agents will have a functionality such as hydrosilyl (—SiH, commonly referred as hydride functions to those the skilled in the art). One preferred conventional catalyst for use in the coatings of the present invention is polymethylhydrosiloxane. Precise control of cross-link density in the coatings of the present invention is achieved by precise control of the ratio of non-cross-linkable silicone polymer (e.g., polydimethylsiloxane) to fully cross-linked polymer. The fully cross-linked polymer is formed by a reaction between the functionalized cross-linkable polymer and the cross-linking agent, for example, a vinylsilylation reaction between vinyl-terminated polydimethylsiloxane and polymethylhydrosiloxane optionally in the presence of a platinum complex catalyst. The ratio between non-cross-linkable polymer, e.g., polydimethylsiloxane, and fully cross-linked polymer is sufficiently effective to provide structural reinforcement to the resulting interpenetrating polymer networks, and is typically between about 0.1 wt./wt. and about 9 wt./wt., preferably between about 0.43 wt./wt. and about 2.33 wt./wt. The vinyl-terminated cross-linkable base polymer, e.g., polydimethylsiloxane base polymer, useful in the coatings of the present invention will have a weight average molecular weight (Mw) of between about 10,000 and about 500,000 and preferably between about 50,000 to about 250,000. Examples of this polymer include, but are not limited to: Gelest Product Code No. DMS-V51, DMS-V52, DMS-V61, DMS-V71, etc., available from Gelest, Inc., Morrisville, Pa. 19067. The typical molecular structure of vinyl terminated polydimethyldisiloxane is the following:

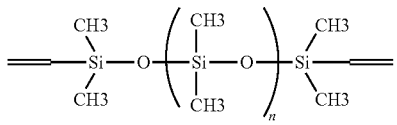

wherein n is defined by the molecular weight.

The cross-linkable siloxane polymer forms the matrix phase of the coating on surface or surfaces of a medical device. Vinyl terminated polydimethylsiloxane reacts with polymethylhydrosiloxane cross-linker in the presence of platinum catalyst under appropriate conditions; the vinyl terminated polydimethylsiloxane linear polymers are fully cross-linked to each other as the result of this reaction. The amount of polymethylhydrosiloxane cross-linker is in large stoichiometric excess compared to vinyl terminated polydimethylsiloxane base polymer. It is believed that the extra SiH functions in the cross-linker react with the OH functions on the surface of the oxide layer of the medical devices, e.g., steel needles, to form Si—O—Fe bonds at elevated temperature. Covalent bonds thus created between the silicone coating and the device or needle surface, as the result of this reaction, result in the adhesive attachment of the coating to the metallic surface.

The polymethyhydrosiloxane cross-linkers, or cross-linking agents, used in the practice of the present invention will have a weight average molecular weight (Mw) between about 1000 and about 3000, and preferably between about 1400 and about 2100. As mentioned previously, the cross-linking agents will have a functionality such as hydrosilyl (—SiH, commonly referred as hydride functions by those the skilled in the art). An example of this polymer cross-linker includes, but is not limited to, Gelest Product Code No. HMS-991, HMS-992, available from Gelest, Inc., Morrisville, Pa. 19607.

The typical molecular structure of the polymethyhydrosiloxane cross-linker is the following:

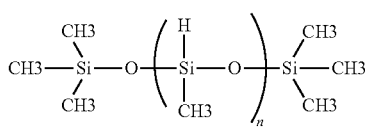

wherein n is defined by the molecular weight.

Polymethylhydro-co-polydimethylsiloxane can also be used as cross-linker or cross-linking agent in the novel coatings of the present invention. Examples of this polymer include, but are not limited to, Gelest Product Code No. HMS-301, HMS-501. The weight average molecular weight of this siloxane polymer cross-linking agent will typically be between about 900 and about 5,000, and preferably about 1,200 to about 3,000. The typical molecular structure of polymethylhydro-co-polydimethylsiloxane cross-linker is the following:

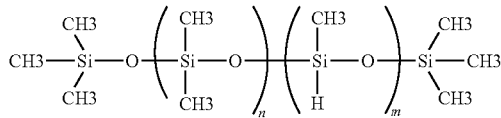

wherein n and m are defined by the molecular weight.

The non-cross-linkable siloxane polymer used in the lubricious coatings of the present invention is preferably trimethylsilyl-terminated polydimethylsiloxane; which is a linear high molecular weight polydimethylsiloxane polymer, and which does not contain reactive functional groups. This polymer provides a non-cross-linked phase in the resulting silicone coating, and is believed to disperse in the matrix phase made from the cross-linked cross-linkable siloxane. The weight average molecular weight of this polymer will typically be between about 400,000 to at least about 10,000,000, more typically about 400,000 to 10,000,000, and preferably between about 400,000 to about 700,000. Examples of this polymer include, but are not limited to, Gelest Product Code No. DMS-T56, DMS-T62, DMS-T61, DMS-D72. The typical molecular structure of the non-cross-linkable siloxane polymer is illustrated below:

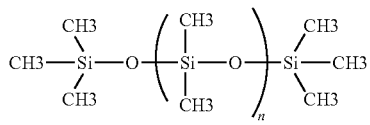

wherein n is defined by the molecular weight.

Catalyst

Bruce Karstedt of GE Silicone invented a highly active platinum catalyst (the "Karstedt catalyst") at the beginning of the 1970's (U.S. Pat. No. 3,775,452). Vinyl-terminated polydimethylsiloxane can react with a polymethylhydrosiloxane cross-linker in less than one minute at ambient temperature with as little as 10 ppm of the Karstedt catalyst. It is typically difficult or impossible to use this catalyst in conventional needle production manufacturing processes because of its high rate of catalytic activity, and since the economics of conventional production processes ideally and typically require up to a one week pot life for the fully catalyzed silicone coating solution. The novel fast curing platinum catalyst of the present invention has been developed to address this issue, and the resulting mixtures of this novel catalyst together with the cross-linkable and non-cross-linkable silicone polymers of the present invention, e.g., vinyl-terminated polydimethylsiloxane and polymethylhydrosiloxane, can be stable at ambient temperatures for more than one week. The cross-linking reaction between the crosslinkable silicone polymer and the cross-linking agent, for example, vinyl-terminated polydimethylsiloxane and polymethylhydrosiloxane, in the presence of the novel catalyst of the present invention can be switched on in less than 10 seconds at elevated temperature. The novel catalyst of the present invention is prepared by reacting the Karstedt catalyst with ethynylcyclohexanol according to Scheme 1 as seen below. The novel catalyst of the present invention provides greater control over curing of the silicone coating solutions. This is conventionally referred to as "command cure".

Scheme 1

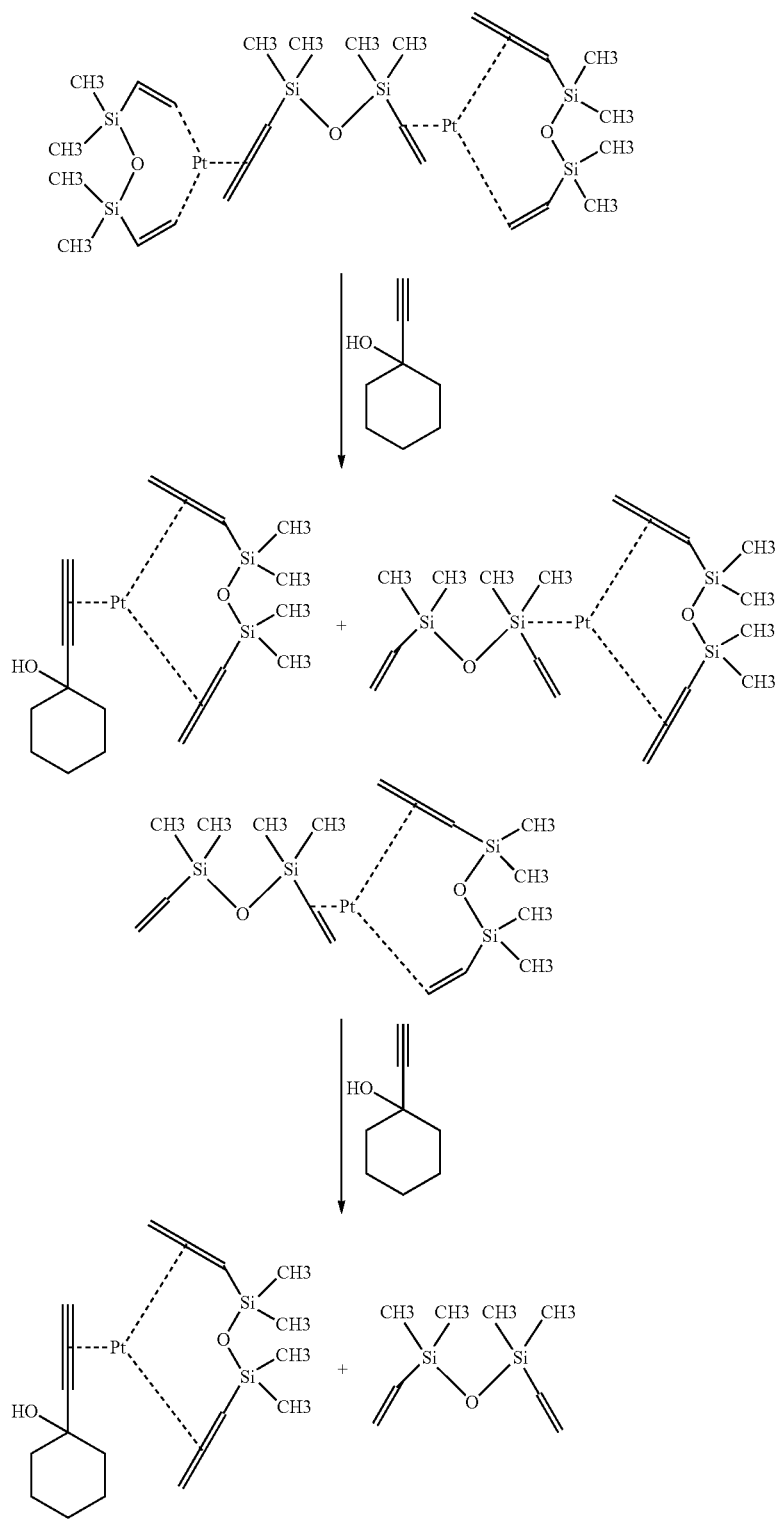

The novel catalyst of the present invention may be prepared in the following manner. Karstedt catalyst in xylene solution is mixed with a low concentration of ethynylcyclohexanol in xylene solution at ambient temperature for a sufficiently effective time to complete the reaction, e.g., a half an hour, and completion of the reaction is indicated by a change of the color of the reaction mixture, from clear to light brown.

The resulting catalyst solution containing the novel catalyst of the present invention is ready to use in the preparation of the lubricious coating solutions of the present invention. The formula of the resulting platinum complex catalyst (platinum divinyltetramethyldisiloxane complex) is:

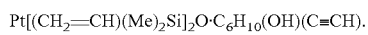

It should be noted that the resulting catalyst reaction mixture will contain a small amount of the reaction product divinyltetramethyldisiloxane. This component does not affect the catalyst, and is a low boiling point component that is rapidly boiled off. Accordingly, purification of the catalyst mixture to remove divinyltetramethyldisiloxane is optional, and it is believe that its presence will not affect the cross-linking reaction of a cross-linkable silicone polymer. The novel catalyst of the present invention is inhibited at low or ambient temperatures and activated at higher or curing temperatures; that is, the catalyst is inactivated at lower or ambient temperatures and activated at higher or curing temperatures. This allows for command cure (command cure catalytic action) of the cross-linkable components in silicone coatings to rapidly form coating films at desired curing temperatures, and provides for long pot life.

Although the novel catalyst of the present invention is preferred and most desirable in the coating compositions of the present invention, it is also possible to use conventional catalysts with these coating compositions. The conventional catalysts include platinum-cyclovinylmethylsiloxane complex (Ashby Karstedt Catalyst), platinum carbonyl cyclovinylmethylsiloxane complex (Ossko catalyst), platinum divinyltetramethyldisiloxane dimethyl fumarate complex, platinum divinyltetramethyldisiloxane dimethyl maleate complex and the like and equivalents.

Solvent and Coating Mixing Procedure

The above-described silicone polymers and platinum catalysts, including the novel platinum complex catalyst of the present invention, are dispersed into organic solvents to form the novel lubricious coating solutions or compositions of the present invention. Both aromatic and aliphatic solvents can be used for the silicone dispersions, however, aromatic solvents are most commonly used for silicone dispersions. Typical examples of useful aromatic solvents include, but are not limited to, xylene and toluene. Aliphatic solvents which are useful include, but are not limited to, pentane, heptanes, hexane and their mixtures. An example of an aliphatic solvent mixture is Exxon Isopar K solvent. The organic solvents are added at a concentration sufficient to provide effective blending of the silicone polymer components into a homogeneous coating solution. The total solvent concentration sufficient to be effective is typically between about 75 wt. % to about 99.5%, and is more typically between about 85 wt. % to about 98.5 wt. %, depending upon the coating thickness requirement. Those skilled in the art will appreciate that the coating thickness can be engineered by changing the solids content of the coating solution.

The following procedure as described utilizes conventional mixing equipment in typical production facilities. The coating compositions of the present invention may be preferably prepared in the following manner. Initially, a suitable organic solvent such as xylene is added to a conventional mixing vessel together with a platinum catalyst and mixed for a sufficiently effective time, for example, up to about 10 minutes to form a solution. Then, a non-cross-linkable silicone polymer component such as trimethylsilyl-terminated polydimethylsiloxane and vinyl-terminated cross-linkable silicone polymer component such as polydimethylsiloxane are dispersed into the solution for a sufficiently effective time; for example, for up to about two hours until fully homogeneous. A suitable organic solvent such as Isopar K solvent is then added to the solution, and the solution is further mixed for a sufficiently effective time, for example, for about one hour prior to the addition of a cross-linking agent such as polymethylhydrosiloxane cross-linker. Then, the cross-linking agent is added to the solution and the solution is fully blended for a sufficiently effective time. The length of such time can be, for example, one additional hour after all of the components have been added to the mixing vessel. Other conventional blending and mixing processes and equipment may be used to manufacture the novel silicone coating compositions of the present invention. For example, the sequence can be modified to some extent when using various other suitably effective conventional mixing equipment, such as a double planetary mixer. All of the components may be mixed in one step in such equipment.

Although not necessarily preferred, in order to reduce VOC emissions, it is possible to formulate the lubricious coating compositions of the present invention in a less volatile organic solvent, an aqueous/organic solvent mixture, or an aqueous solvent solution. This can be done by done in a conventional manner similar to that used for low VOC polymeric coatings.

In the following paragraph, the wt. % is the wt. % of total solids content in the coating solution. The novel coating compositions of the present invention will contain sufficient amounts of the polymeric components, cross-linking agent, catalyst, and solvent to effectively provide a silicone coating having high lubricity and durability, a long pot life, and suitable for application in conventional coating processes using conventional coating equipment. Typically, the amount of the non-cross-linkable silicone polymer will be about 10 wt. % to about 90 wt. % (total solids), more typically about 30 wt. % to about 70 wt. % (total solids), and preferably about 40 wt. % to about 60 wt. % (total solids). The amount of the cross-linkable silicone polymer will typically be about 10 wt. % to about 90 wt. % (total solids), more typically about 30 wt. % to about 70 wt. % (total solids), and preferably about 40 wt. % to about 60 wt. % (total solids). An excess amount of silicone cross-linking agent will be used in the process and coatings of the present invention. For purposes of the present invention an excess amount of cross-linking agent is defined to mean excess amount of cross linking functions (hydrosilyl functions, —SiH) against cross linkable functions (—Si(CH=CH$_2$) in cross linkable polymer vinyl terminated polydimethylsiloxane in stoichiometry mole ratio. The preferred mole ratio of cross linking functions (—SiH) to cross linkable functions (—SiCH=CH$_2$) is in the range between 10 to 70. The amount of the silicone cross-linking agent will typically be about 0.2 wt. % to about 6 wt. % (total solids), more typically about 0.3 wt. % to about 4 wt. % (total solids), and preferably about 0.45 wt. % to about 3 wt. % (total solids). It is surprising and unexpected, and contrary to the teaching in this art, that using an excess amount of silicone cross-linking agent could result in the durable coatings produced by the method of the present invention because an excess of cross linking-functions remains after cure which affects the mechanical properties of the silicone over time. Also, a large excess of cross linking functions is conventionally believed to have an adverse effect on the pot life of the silicone prior to its curing process. The amount of the platinum catalyst based upon the total solids in the novel lubricious silicone coating compositions (platinum element in total solids) of the present invention will typically be about 0.0004 wt. % to about 0.0036 wt. %, more typically about 0.0012 wt. % to about 0.0028 wt. %, and preferably about 0.0016 wt. % to about 0.0024 wt. %.

The amount of organic solvent in the coating compositions of the present invention will typically be about 75 wt. % to about 99.5 wt. %, more typically about 28 wt. % to about 99 wt. %, and preferably about 15 wt. % to about 98.5 wt. %. Those skilled in the art will appreciate that the amount of solvent present in the novel coating compositions of the present invention will vary with several factors, and that the solvent quantity in the coating compositions will be selected to engineer an efficacious coating. The factors typically considered include the method of application, the method of cure, the coating equipment utilized, ambient conditions, thickness, etc. It will be appreciated that each of the components of the coating compositions of the present invention may consist of blends of those components. For example, two or more different molecular weight non-cross-linkable silicone polymers may be used, or two or more cross-linkable silicone polymers having different functionalities and/or molecular weights may be used, etc.

Coating Process

The novel silicone lubricious coating compositions of the present invention are applied to one or more surfaces of a medical device, such as a surgical needle, using conventional coating techniques and processes and conventional coating equipment. One example of coating equipment that can be used to apply the coatings includes, but is not limited to, simple dip coating tanks and in-line convection ovens for curing. The coating compositions can also be applied by conventional brushing, rolling, or spraying processes, and any equivalent processes. The vinyl silylation addition cross-linking reaction can be completed (i.e., the coating can be cured) in-line by passing the coated device through a heating oven for a sufficiently effective time. The curing times will vary, for example, from about 5 seconds to about one hour, and will vary with respect to parameters such as the cross-linker concentration, catalyst concentration, coating thickness, ambient conditions, device construction and material type, etc. However, the cure times can be as short as about 20 seconds at 450° C., or about 6 seconds at 600° C. Flash cure (i.e., instantaneous or rapid cure) can also be achieved with the present lubricious silicone coating containing the novel catalyst of the present invention. Other conventional curing techniques which can be utilized with the novel silicone coating compositions of the present invention include thermal (e.g., convection heating), ultraviolet light, plasma, microwave radiation, electromagnetic coupling, ionizing radiation, laser, and the like. Prior to coating, the surfaces of the medical devices will be prepared in a conventional manner using conventional processes such as electro-polishing, oxidation, ultrasonic cleaning, plasma etch, chemical cleaning, and the like. If desired, a batch coating and curing process can also be used rather than an in-line process.

Gamma Radiation Curing

The silicone coatings on the surfaces of medical devices produced by the novel process of the present invention are treated after curing with gamma radiation. The dose of gamma radiation that the coated medical devices are exposed to after curing will be sufficient to effectively provide an improved or flat penetration force profile for the medical device, for example, a flat penetration force profile for a coated surgical needles after 100 penetrations. The amount radiation and the duration of the radiation exposure will depend on several factors including the rate of dosage and the length of dosing time. The minimum amount of gamma irradiation exposure will be at least 25 kilogray (kGy), and the typical amount of gamma irradiation exposure will 40 kilogray (kGy). The needles will be placed into conventional gamma radiation treatment equipment, for example a Gammacell gamma radiation device, Model No. 220E. Conventional radiation measuring instrumentation may be used to measure the radiation dose. For example, conventional dosimeters may be used.

Test Procedures for Coating Performance

Coating performance for medical devices coated with the novel compositions of the present invention can be tested with a variety of conventional friction or adhesion tests. In the case of surgical needles, coating performance, durability and integrity are evaluated using a conventional needle penetration testing apparatus. A coated surgical needle is held using a mounting fixture on the apparatus, such as self-locking tweezers or a similar holding device. The coated needle is then passed through a polymeric medium by the apparatus; the polymeric medium is selected to be representative of general human tissue. Typically, approximately half of the needle length is passed through the medium and then retracted prior to the next pass. The test media may be a type of synthetic rubber (e.g., Duraflex™, manufactured by Monmouth Rubber and Plastic Corporation, Monmouth, N.J.). The needle can be passed through the penetratable material typically for about one to about twenty times, more typically between about one to about twenty-five times, and most preferably between about one to about thirty times. The needle is then retracted from the media. The maximum force is recorded for each pass and is used as a measure of the coating performance. Various attributes of coating performance can be tested using these techniques, including durability and lubricity.

A typical test includes using 10 needles that are individually passed through the media 100 times each. The maximum force is recorded for each pass and used as a measure of the coating performance. Typically the penetration force increases with each successive pass as the coating wears off from the needle.

As mentioned previously above, the medical devices that may be coated with the novel method and lubricious coatings of the present invention include conventional medical devices such as surgical needles, hypodermic needles, catheters, surgical probes, endoscopes, syringes, scalpels, cutting blades, orthopaedic implants, trocars, cannulas, and the like. The medical devices will be constructed from conventional biocompatible materials including surgical stainless steels, PTFE, glass, alloyed steels, refractory metal alloys, memory alloys, polymers, composites comprising metallic and non-metallic components ingredients, combinations thereof, and the like. The biocompatible materials may include nonabsorbable materials and bioabsorbable materials. The devices that may be coated by the novel process of the present invention may be used advantageously in robotic surgical procedures with robotic surgical units, wherein durable and lubricious coatings are required. Particularly advantageous for robotic applications is the invariant tissue penetration force of the present inventive coatings and the resilience of the inventive coatings in response to being abraded during suturing. Similarly, such coated devices are advantageously useful for medical devices used in minimally invasive procedures such as laparoscopic and endoscopic procedures, where surgical instruments and medical devices must repeatedly pass through narrow passages such as trocar cannulas to remotely access the surgical site. The coated medical devices of the present invention also fulfill an unmet need in reusable medical devices that need to retain a lubricious and durable coating after repeated cleanings and sterilizations, e.g., eyed surgical needles, laparoscopic cutters and graspers, robotic end effectors and robotic surgical instruments, etc.

The following examples are illustrative of the principles and practice of the present invention, although not limited thereto:

Example 1

This example provide needle coating solution with a mixture of the silicone components summarized in Table 1.

TABLE 1

Coating Formulation.

| Component | Trade Name | Weight (g) |
|---|---|---|
| Trimethylsilyl terminated polydimethysiloxane | Gelest DMS T72 | 1200 |
| dimethylvinyl silyl terminated polydimethysiloxane | Gelest DMS V52 | 1200 |
| Platinum catalyst 0.01% solution | | 480 |
| Trimethylsilyl terminated polymethylhydrosiloxane | Gelest DMS HMS 991 | 24 |
| Solvent 1 | Xylene | 5096 |
| Solvent 2 | Exxon Isopar K | 8783 |

The above components were mixed together in a high shear mixer at a speed of 30 Hz for 4 hour.

Example 2

Three types of cardio needles (Ethicon, Inc.) were selected for this example:

12 mil RB-2
16 mil RB-1
26 mil SH

Strips of needles were dipped into the mixture of silicones in the solution summarized in Table 1 (refer as new silicone after here) in a dip tank. The excess coating solution on the needles was removed using a blow-off device disclosed in U.S. Pat. No. 8,883,245. The pressure on the blow off device was set at 20 psi. The coated needles were heated at 195° C. for 120 minutes in a conventional convection oven.

The resulting coated needles are labeled as: 2a (12 mil RB-2); 2b (16 mil RB-1); 2c (26 mil SH)

Half of the coated needles were subjected to gamma irradiation in a conventional radiation unit (Gammacell, Model 220E, serial #193R) at 40 kGy and the resulting needles are labeled as: 2a Gamma (12 mil RB-2); 2b Gamma (16 mil RB-1); 2c Gamma (26 mil SH)

Penetration testing was performed on these six sets of needles as described in the testing section. The results are from penetration testing done using 10 individual needles. The coated needles were penetrated 100 times each. The average penetration force for each pass is summarized in Table 2-1 to 2-3. The data is presented graphically in FIG. 1.

The control samples were also prepared for the purpose of comparison. The same three sets of needles were coated with Nusil MED 4162 (commercially available from Nusil Technology LLC, Carpinteria, Calif.) and processed in the same manner as the other needles in Example 2 listed in the paragraph above. The needle penetration testing results are also included in Tables 2-1 to 2-3.

TABLE 2-1

Needle Penetration Test: 12 mil RB-2 Needles.

| Penetration# | Example 2a with gamma (g) | Control* Nusil (without gamma) (g) |
|---|---|---|
| 1 | 42 | 46 |
| 10 | 40 | 70 |
| 20 | 41 | 80 |
| 25 | 41 | 85 |
| 50 | 44 | 101 |
| 75 | 47 | 109 |
| 100 | 49 | 113 |

TABLE 2-2

Needle Penetration Test: 16 mil RB-1 Needles.

| Penetration# | Example 2b without Gamma (g) | Example 2b with Gamma (g) | Control 1 Nusil without Gamma (g) | Control 2 Nusil with gamma (g) | Uncoated Needles (g) |
|---|---|---|---|---|---|
| 1 | 50 | 71 | 55 | 62 | 135 |
| 10 | 54 | 65 | 83 | 83 | 130 |
| 20 | 58 | 64 | 95 | 97 | 135 |
| 25 | 60 | 65 | 99 | 102 | 132 |
| 50 | 65 | 67 | 113 | 116 | 132 |
| 75 | 70 | 69 | 119 | 118 | 125 |
| 100 | 73 | 71 | 123 | 121 | 125 |

TABLE 2-3

Needle Penetration Test: 26 mil SH Needles.

| Penetration# | Example 2c without Gamma (g) | Example 2c with Gamma (g) | Control 1 Nusil (Without Gamma) (g) | Control 2 Nusil (with Gamma) (g) |
|---|---|---|---|---|
| 1 | 77 | 100 | 65 | 92 |
| 10 | 85 | 95 | 88 | 115 |
| 20 | 90 | 95 | 107 | 127 |
| 25 | 93 | 93 | 113 | 130 |
| 50 | 105 | 95 | 133 | 135 |
| 75 | 110 | 105 | 135 | 145 |
| 100 | 112 | 98 | 150 | 152 |

The sizes and shapes of the needles used in this example are different from each other, yet the same conclusion was found on their penetration durability. The penetration performance of the needles coated by the inventive method remains constant over hundred repeat passes. This means a consistent tactile response from the needles to the hand of the surgeon during a lengthy closure process, rather than an unpredictably increasing force required for penetration, such as those current commercial products shown in the tables above as control samples, in which the penetration forces of the current product increase up to 2.46 times during the course of 100 penetrations.

Example 3

This example provided needle coating solutions with a mixture of components identical to Example 1, except the loading of cross-linker trimethylsilyl terminated polymethylhydrosiloxane Gelest HMS 991. Four levels of cross-linker loading were tested in this example and the amount of each level is summarized in Table 3. The amount of cross-linker in Example 1 is also included in this table. Cross-linker Gelest HMS991 has a formula of $(CH_3)_3Si$—O—[—$(CH_3)_3SiH$—O-]$_n$-Si$(CH_3)_3$ with a molecular weight around 1600. 24 —SiH functions present in each molecule of this cross linker (n=24). The cross-linkable polymer in example 1 dimethylvinyl silyl terminated polydimethysiloxane (Gelest DMS V52) has a formula of $(CH_3)_2(CH_2$═$CH)Si$—O—[—$(CH_3)_2Si$—O-]$_n$-Si$(CH_3)_2(CH$═$CH_2)$ with molecular weight around 155,000. 2 —Si(CH═CH$_2$) functions present in each molecule of this cross linkable polymer. The mole ratio calculations in Table 3 were based on this.

TABLE 3

Amount of Cross-Llinker Gelest HMS 993 and its Excess Mole Ratio Against Vinyl

| Example | Weight (g) | Excess Mole Ratio |
|---|---|---|
| 3a | 3.13 | 2 |
| 3b | 7.30 | 6 |
| 3c | 12.52 | 11 |
| 3d | 69.91 | 66 |
| 1 | 24 | 22 |

The above components were mixed together in a high shear mixer at a speed of 30 Hz for 4 hours.

Example 4

A strip of 16 mil RB-1 needles (Ethicon, Inc.) was dipped into silicone solutions summarized in Table 3 in a dip tank. The excess coating solution on the needles removed using the previously-mentioned blow-off devices. The pressure on the blow off devices was set at 20 psi. The coated needles were heated at 195° C. for 120 minutes in a conventional convection oven.

The resulting coated needles were labeled as: 4a (coated with Example 3a); 4b (coated with example $b); 4c (coated with Example 3c); and, 4d (coated with Example 3d).

Half of the coated needles were subjected to gamma irradiation at 40 kGy using the previously-described equipment and the resulting needles are labeled as: 4a Gamma (coated with example 3a); 4b Gamma (coated with Example 3b); 4c Gamma (26 mil SH coated with example 3c); and, 4d Gamma (26 mil SH coated with Example 3d).

Penetration testing was performed on these six sets of needles as described in the testing section. The results are from penetration testing done using 10 individual needles. The coated needles were penetrated 100 times each. The average penetration force for each pass is summarized in Tables 4-1 and 4-2.

The needle penetration testing results of example 2b and 2b gamma are also included in the Tables.

TABLE 4-1

Needle Penetration Test on 16 mil RB-1 Needles of Example 4.

| Example | 1$^{st}$ Pass (g) | 10$^{th}$ Pass (g) | 20$^{th}$ Pass (g) | 25$^{th}$ Pass (g) | 50$^{th}$ Pass (g) | 75$^{th}$ Pass (g) | 100$^{th}$ Pass (g) |
|---|---|---|---|---|---|---|---|
| 4a (2X excess) | 33 | 59 | 76 | 82 | 101 | 111 | 118 |
| 4b (6X excess) | 31 | 43 | 47 | 51 | 76 | 90 | 99 |
| 4c (11X excess) | 30 | 40 | 51 | 55 | 71 | 83 | 92 |
| 4d (66X excess) | 38 | 41 | 44 | 46 | 52 | 57 | 61 |
| 2b (22X excess) | 50 | 54 | 58 | 60 | 65 | 70 | 73 |

TABLE 4-2

Needle Penetration Test on 16 mil RB-1 Needles of Gamma Irradiated Example 4.

| Example | 1$^{st}$ Pass (g) | 10$^{th}$ Pass (g) | 20$^{th}$ Pass (g) | 25$^{th}$ Pass (g) | 50$^{th}$ Pass (g) | 75$^{th}$ Pass (g) | 100$^{th}$ Pass (g) |
|---|---|---|---|---|---|---|---|
| 4a (2X excess) Gamma | 52 | 56 | 70 | 75 | 101 | 121 | 126 |
| 4b (6X excess) Gamma | 53 | 54 | 93 | 107 | 123 | 128 | 130 |
| 4c (11X excess) Gamma | 46 | 48 | 50 | 52 | 58 | 63 | 67 |
| 4d (66X excess) Gamma | 61 | 57 | 56 | 56 | 58 | 65 | 67 |
| 2b (22X excess) Gamma | 71 | 65 | 64 | 65 | 67 | 69 | 71 |

It was found and observed, surprisingly and unexpectedly, in Examples 4c, 4d and 2b that the penetration performance of the gamma irradiated needles remained largely constant over one hundred repeat passes. Between 11 to 66 time excess in the mole ratio of —SiH to —Si(CH═CH$_2$) is required to achieve this desire penetration performance, as seen in these three examples.

The novel coating method of the present invention and resulting coatings and coated medical devices of the present invention have many advantages compared with the coatings and catalysts of the prior art. The advantages include that the penetration performance of surgical needles coated by this method remains constant over at least one hundred repeat passes. This means a consistent tactile response from the needles to the hand of the surgeon during a lengthy closure process, rather than an unpredictably increasing force required for penetration. The method of the present invention producing durable lubricious coatings is additionally particularly advantageous for instruments and devices (including surgical needles) and end effectors used in robotic surgery. The novel method of the present invention also provides reusable devices having durable coatings that remain lubricious and durable after repeated cleaning and sterilization cycles. The devices coated with the novel process of the present invention are also particularly useful in minimally invasive surgical techniques such as laparoscopic, endocsopic, and arthroscopic where durable lubricious coatings enhance the surgical procedures, for example by allowing the instruments to be repeatedly and readily inserted through access ports and cannulas while retaining lubricity and coating integerity, thus facilitating the surgical procedures.

Although this invention has been shown and described with respect to detailed embodiments thereof, it will be understood by those skilled in the art that various changes in form and detail thereof may be made without departing from the spirit and scope of the claimed invention.

We claim:

1. A method of coating a surface of a medical device with a lubricious, silicone coating composition, comprising the steps of:
   A. applying a lubricious silicone coating composition to a surface of a medical device, the silicone coating composition comprising:
   a cross-linkable silicone polymer having first reactive functionalities;
   about 10 wt. % to about 90 wt. % of a non-cross-linkable silicone polymer, based on total solids, wherein said polymer has a weight average molecular weight between about 400,000 and 10,000,000;
   an excess of amount of about 0.2 wt. % to about 6 wt. % of a silicone cross-linking agent having second reactive functionalities based on total solids, wherein said second reactive functionalities are present in excess to said first reactive functionalities; and, a catalyst, wherein said catalyst consists essentially of platinum divinyltetramethyldisiloxane ethynylcyclohexanol complex having the formula:

$Pt[(CH_2\!=\!CH)(Me)_2Si]_2O\cdot C_6H_{10}(OH)(C\!\equiv\!CH)$, wherein said composition has a weight;
   B. curing the coating; and;
   C. exposing the medical device and cured coating composition to a sufficient dose of gamma radiation for a sufficient period of time to effectively provide a flat penetration force profile wherein the profile does not vary more than about +/−10% from the initial penetration force for up to 20 penetrations.

2. The method of claim 1, wherein the cross-linkable silicone polymer is selected from the group consisting of vinyl terminated: polydialkylsiloxane, polydimethylsiloxane, polydiphenylsilane-dimethylsiloxane copolymer, polyphenylmethylsiloxane, polyfluoropropylmethyl-dimethylsiloxane copolymer and polydiethylsiloxane.

3. The method of claim 1, wherein the cross-linkable silicone polymer comprises vinyl terminated polydimethylsiloxane.

4. The method of claim 1, wherein the non-cross-linkable silicone polymer is selected from the group consisting of polydimethyl siloxane, polyalkylmethylsiloxane, polydiethylsiloxane, polyfluoropropylmethylsiloxane, polyoctylmethylsiloxane, polytetradecylmethylsiloxane, polyoctadecylmethylsiloxane, polyalkylmethyl dimethylsiloxane, and polyhexadecymethylsiloxane-dimethyl sioxane.

5. The method of claim 1, wherein the non-cross-linkable silicone polymer comprises trimethylsilyl terminated polydimethylsiloxane.

6. The method of claim 1, wherein the cross-linking agent is selected from the group consisting of polymethylhydro siloxane, polymethylhydro-co-polydimethylsiloxane, polyethyhydrosiloxane, polymethylhydrosiloxane-co-octylmethylsiloxane, and polymethylhydrosiloxane-co-methylphenylsiloxane.

7. The method of claim 1, wherein the cross-linking agent comprises polymethylhydrosiloxane.

8. The method of claim 1, wherein the composition comprises about 10 wt. % to about 90 wt. % of the cross-linkable silicone polymer, based on total solids wherein the composition additionally comprises about 75 wt. % to about 99.5 wt. % of an organic solvent, based upon the weight of the coating composition.

9. The method of claim 1, wherein the composition comprises about 0.45 wt. % to about 3 wt. % of the silicone cross-linking agent, based on total solids, wherein the composition additionally comprises about 75 wt. % to about 99.5 wt. % of an organic solvent, based upon the weight of the coating composition.

10. The method of claim 1, wherein the composition comprises about 0.0004 wt. % to about 0.0036 wt. % of the catalyst, based on total solids, wherein the composition additionally comprises about 75 wt. % to about 99.5 wt. % of an organic solvent, based upon the weight of the coating composition.

11. The method of claim 1, wherein the composition additionally comprises a solvent selected from the group consisting of xylene, toluene, pentane, hexane, heptanes, octane, Isopar K, and combinations thereof.

12. The method of claim 1, wherein the first reactive functionalities comprises hydrosilyl group (—SiH).

13. The method of claim 1, wherein the second reactive functionalities comprises vinylsilyl group (Si(CH═CH2)).

14. The method of claim 1, wherein the excess amount of cross-linking agent comprises hydrosily group with between 10 to 70 times of vinylsilyl group (Si(CH═CH2)).

15. The method of claim 1, wherein the coating is cured by exposing the coating to an energy source selected from the group consisting of thermal, ultraviolet light, plasma, microwave radiation, electromagnetic coupling, ionizing radiation and laser.

16. The method of claim 1, wherein the medical device comprises a surgical needle.

17. The method of claim 1, wherein the medical device comprises a robotic instrument.

18. A medical device, said device comprising a surface coated by the method of claim 1.

19. A surgical needle coated by the process of claim 1, wherein the surgical needle has a flat penetration force profile after 100 passes through tissue or tissue simulation media.

20. A robotic surgical instrument, comprising a surface coated by the method of claim 1.

21. The method of claim 1 wherein the profile does not vary more than about +/−10% from the initial penetration force for up to 100 penetrations.

22. The method of claim 1 wherein the profile does not vary more than about +/−10% from the initial penetration force for up to 50 penetrations.

* * * * *